United States Patent [19]
Giesen et al.

[11] Patent Number: 4,826,809

[45] Date of Patent: May 2, 1989

[54] ADDITIVE FOR COSMETIC PREPARATIONS

[75] Inventors: Monika Giesen, Weinheim; Magdalene Hubbuch, Schriesheim, both of Fed. Rep. of Germany

[73] Assignee: Firma Carl Freudenberg, Weinheim/Bergstr, Fed. Rep. of Germany

[21] Appl. No.: 884,970

[22] Filed: Jul. 14, 1986

[30] Foreign Application Priority Data

Aug. 6, 1985 [DE] Fed. Rep. of Germany ....... 3528168

[51] Int. Cl.$^4$ .......................... A61K 37/02; A61K 7/48
[52] U.S. Cl. .......................................... 514/2; 530/350; 514/773; 514/777; 514/844
[58] Field of Search ............... 514/844, 845, 846, 847, 514/848, 2, 8, 773, 783, 777; 424/58, 195.1

[56] References Cited

U.S. PATENT DOCUMENTS

| | | | |
|---|---|---|---|
| 3,659,025 | 4/1972 | Halleck | 514/777 |
| 3,972,997 | 8/1976 | Nakashio et al. | 514/844 X |
| 4,130,667 | 12/1978 | Smith | 514/947 X |
| 4,668,772 | 5/1987 | Lee | 530/407 |

FOREIGN PATENT DOCUMENTS

| | | | |
|---|---|---|---|
| 2382891 | 11/1978 | France | 514/777 |
| 2297033 | 8/1986 | France . | |
| 13705 | 1/1984 | Japan | 514/773 |

OTHER PUBLICATIONS

Chemical Abstracts, 98, (1983), 132155 n, (Nisshin Oil Mills, Ltd.).
Chemical Abstracts, 100, (1984), 179945 v, (Nisshin Oil Mills, Ltd.).
Cosmetic and Perfumery, 89, (Apr. 1974), pp. 45-48.
Waggle et al., "Soy Protein and Human Nutrition", Academic Press Inc., (1979), p. 30.
Brooks Industries Inc., Cosmetic Counter Tale, Aug. 1984.

Primary Examiner—John S. Maples
Attorney, Agent, or Firm—Felfe & Lynch

[57] ABSTRACT

Disclosed is an additive containing vegetable protein hydrolyzates for cosmetic preparations. The additive consists mostly of protein components having molecular weights greater than 10,000 and short-chain protein components as well as mono-, di- and/or oligosaccharides.

2 Claims, No Drawings

ADDITIVE FOR COSMETIC PREPARATIONS

BACKGROUND OF THE INVENTION

The present invention relates to an additive containing vegetable protein hydrolyzates for cosmetic preparations.

Cosmetic preparations can be divided roughly into two types:

(a) Tenside-containing preparations having principally a cleaning action, (b) Skin-care cosmetic preparations.

Both kinds must contain components which exercise a protective function on the skin of the user. In the case of the first type of preparation, the components are intended to mitigate or prevent the negative phenomena accompanying tensides, namely excessive soil removal, destruction of the acid environment of the skin, and the occurrence of roughness on the skin surface. In the second type of cosmetic preparation, the action of the additives is characterized by the formation of a protective film, e.g. against external influences on the skin.

For the above-named purposes, animal protein hydrolyzates, for example, are used. They have a good solubility in water, but often, even in the presence of tensides, they do not have a sufficient foam stabilizing action. It must also be considered a disadvantage that these additives are not soluble in alcohol; their application in alcohol-containing preparations is thus limited. A third deficiency is that animal protein hydrolyzates alone, without additives, do not have any kind of moisture-preserving properties.

The use of protein hydrolyzates of vegetable origin as additives for cosmetics is likewise known. They are offered to the cosmetic industry, for example, by Brooks Industries, Inc., U.S.A. (1985). They are obtained chiefly from soya. Their molecular weights run around 1000. Cosmetic products containing these ingredients, however, are lacking in foam stability, good foam formation and sudsing ability. They have no film-forming properties and hence no moisture-preserving properties, rendering them of no interest for use in preparations for skin care.

The present invention therefore addresses the problem of devising an additive for cosmetic preparations which is to contain protein hydrolyzates and which is to have a wide range of usefulness. For this purpose, it must be easily soluble in water and also in alcohols to at least 30 percent by weight. In addition, it must combine good foam formation, good foam stabilization and good sudsing ability in the presence of even small amounts of tensides. As regards its effectiveness, it is to have film-forming properties and skin moisturizing properties. The sum of these physical and physiological properties would make this additive containing vegetable hydrolyzates universally useful both in cleansing and in skin-care cosmetics.

THE INVENTION

The present invention is in an additive for cosmetic preparations which overcomes the above drawbacks of the prior art. The additive for cosmetic preparations consists of vegetable protein hydrolyzates being expressed as a percentage by weight of the dry mass, 45 to 75% vegetable protein components having molecular weights greater than 10,000 and 20 to 40 weight-percent of vegetable protein components having molecular weights of less than 8,000, together with 5 to 20 weight-percent of a variety of mono-, di- and oligosaccharides. Crucial to its effectiveness is evidently the unusually high molecular weight of the vegetable protein component which is its principal component.

The effectiveness of the additive is further increased by the short-chain protein fragments of molecular weights lower than 8000 which are present in lower concentrations.

The mono-, di- and oligosaccharides obtained by starch degradation, especially glucose and maltose, in the amounts according to the invention of 5 to 20 percent by weight, produce a further improvement of the film-forming and moisturizing ability of the composition. Further suitable monosaccharides are fructose, galactose, ribose, arabinose.

The additive of the invention is incorporated into the cosmetic preparations in amounts of 0.1 to 10% by weight and preferably in amounts of 1 to 5 wt.-%. The additive can be utilized in a dry form such as a dry powder, or as an aqueous phase having a dry content of from 10 to 50 wt.-%, for liquid, gel-like cosmetics or pastes.

DESCRIPTION OF A PREFERRED EMBODIMENT

Vegetable protein hydrolyzates can be obtained from cereals, oil seeds and other vegetable materials, such as soybean, wheat, almonds and sun flowers. Vegetable hydrolyzates can be produced by controlled enzymatical degradation. All parts of vegetable can be used for hydrolyzation, preferably seeds and fruits. The enzymes are, for example, proteases or pectinases. The vegetable precursor, in this example wheat-gluten, is reduced to small pieces, and the enzyme or enzymes, in this example trypsin, together with an excess of water are added. The suspension is heated to about 50° to 80° C. with stirring. The hydrolyzation is finished after some minutes or days, according to the kind of vegetable used. The liquid phase, that is the hydrolyzate, is then separated from the remaining solid particles.

The composition of an additive according to the invention will be described below by means of an example. Also, its universal usefulness in a variety of cosmetics will be made clear.

| Protein content (N × 6.25), total (in the following molecular weight ranges: | 84 weight-percent |
|---|---|
| >10,000 | 55 wt. % |
| <8,000 | 32 wt. %) |
| Saccharides (glucose, maltose, oligosaccharides) | 7 wt. % |
| Residual moisture | 7 wt. % |
| Ash | 2 wt. % |

This additive was incorporated into different cosmetic preparations in the following amounts:

| Shower gel | 3% |
|---|---|
| Alcohol-base, aftershave lotion | 1% |
| Dentrifrice | 2% |
| Creme masque | 5% |

All these products were of high quality as regards their required characteristics:

| |
|---|
| Foam stability (shower gel, dentrifice) |
| Film formation (after-shave lotion) |
| Moisturization (creme masque) |

FOAM STABILITY

The product is filled into a glass cylinder, shaken well for a period of time, and then the fall down (collapse) of the foam within a definite period of time is observed.

FILM FORMATION

The liquid is poured onto a glass slide and dried under vacuum. It is observed, if the residue is a film or a powder.

MOISTURIZATION

The moisture content of the skin surface is tested by an electrode being able of measuring the conductivity of a defined area.

It is therefore possible with an additive according to the invention to cover a broad range of cosmetics.

It will be understood that the specification and examples are illustrative but not limitative of the present invention and that other embodiments within the spirit and scope of the invention will suggest themselves to those of ordinary skill in the art.

We claim:

1. An additive for a cosmetic preparation, comprising vegetable protein hydrolyzates, said hydrolyzates being expressed as a percentage by weight of dry mass, 45 to 75% vegetable protein components having molecular weights greater than 10,000, and 20 to 40 weight-percent vegetable protein components having molecular weights of less than 8,000; and 5 to 20 weight-percent of a variety of mono-, di- and oligo-saccharides.

2. A cosmetic preparation containing 0.1 to 10 wt.-% of the additive of claim 1.

* * * * *